(12) United States Patent
Wenchell

(10) Patent No.: US 8,062,305 B2
(45) Date of Patent: Nov. 22, 2011

(54) SURGICAL PORTAL WITH ENHANCED RETENTION CAPABILITIES

(75) Inventor: Thomas Wenchell, Durham, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 280 days.

(21) Appl. No.: 11/081,183

(22) Filed: Mar. 16, 2005

(65) Prior Publication Data
US 2006/0212061 A1    Sep. 21, 2006

(51) Int. Cl.
*A61B 17/34* (2006.01)
(52) U.S. Cl. .................. 606/108; 606/185; 600/184
(58) Field of Classification Search .............. 604/174, 604/263, 264, 273, 275, 272, 164.04, 164.11, 604/164.12, 523, 43, 164.01, 164.07, 506; 606/108, 1, 185, 184, 191–200, 232; 411/52, 411/69–74, 160–163, 387.5, 416, 442, 451.3, 411/451.4, 456, 466, 467, 468, 451.1, 451.5; 600/184
See application file for complete search history.

(56) References Cited

U.S. PATENT DOCUMENTS

| | | | | |
|---|---|---|---|---|
| 942,693 | A | * | 12/1909 | Wintermute, M.W. ....... 403/276 |
| 1,774,846 | A | * | 9/1930 | Rosenberg ..................... 411/457 |
| 2,650,516 | A | * | 9/1953 | Poupitch ....................... 411/508 |
| 4,655,752 | A | | 4/1987 | Honkanen et al. |
| 5,147,316 | A | | 9/1992 | Castillenti |
| 5,217,441 | A | | 6/1993 | Shichman |
| 5,226,890 | A | | 7/1993 | Ianniruberto et al. |
| 5,234,455 | A | | 8/1993 | Mulhollan |
| 5,472,429 | A | | 12/1995 | Yoon |
| 5,697,913 | A | * | 12/1997 | Sierocuk et al. ......... 604/164.11 |
| 5,782,813 | A | | 7/1998 | Yoon |
| 5,792,112 | A | | 8/1998 | Hart et al. |
| 5,817,062 | A | * | 10/1998 | Flom et al. .................... 604/174 |
| 5,824,002 | A | * | 10/1998 | Gentelia et al. .......... 604/164.11 |
| 5,904,699 | A | | 5/1999 | Schwemberger et al. |
| 5,957,888 | A | | 9/1999 | Hinchliffe |
| 6,004,302 | A | * | 12/1999 | Brierley ........................ 604/264 |

(Continued)

FOREIGN PATENT DOCUMENTS
EP    0 823 241 A    2/2004
(Continued)

OTHER PUBLICATIONS

European Search Report for EP 06004712, date of completion is Jun. 7, 2006 (8 pgs).

*Primary Examiner* — Kathleen Sonnett

(57) ABSTRACT

A surgical portal apparatus for permitting introduction of a surgical object within tissue includes a portal member defining a longitudinal axis and having leading and trailing ends. The portal member includes an outer wall defining a longitudinal opening dimensioned for reception of a surgical object. At least one projection is disposed on the outer wall of the portal member and extends in at least a radial direction relative to the longitudinal axis. The at least one projection is dimensioned and configured for engaging tissue to resist movement of the portal member within tissue. The at least one projection defines a recess for receiving tissue portions adjacent thereto. A plurality of projections is spaced about the outer wall of the portal member. At least two of the projections are circumferentially spaced relative to the longitudinal axis and/or at least two of the projections are longitudinally spaced relative to the longitudinal axis.

18 Claims, 4 Drawing Sheets

U.S. PATENT DOCUMENTS

| | | |
|---|---|---|
| 6,017,356 A | 1/2000 | Frederick et al. |
| 6,146,387 A | 11/2000 | Trott et al. |
| 6,221,060 B1 * | 4/2001 | Willard .......................... 604/264 |
| 6,315,770 B1 * | 11/2001 | de la Torre et al. ................ 606/1 |
| 6,432,085 B1 * | 8/2002 | Stellon et al. ............ 604/164.04 |
| 6,726,664 B2 * | 4/2004 | Yaron et al. ................... 604/265 |
| 7,468,068 B2 * | 12/2008 | Kolster ......................... 606/228 |
| 2004/0087914 A1 | 5/2004 | Bryan et al. |

FOREIGN PATENT DOCUMENTS

| | | |
|---|---|---|
| WO | WO 99/26567 | 6/1999 |
| WO | WO 00/54678 | 9/2000 |

* cited by examiner

SURGICAL PORTAL WITH ENHANCED RETENTION CAPABILITIES

BACKGROUND

1. Field of the Disclosure

The present disclosure generally relates to surgical instruments for performing laparoscopic and endoscopic surgical procedures, and, more particularly, relates to a surgical portal incorporating a novel retention mechanism for resisting slippage of and retropulsion of the portal during use in a highly pressurized environment.

2. Description of the Related Art

In laparoscopic and endoscopic surgical procedures, a small incision or puncture is made in the patient's body to provide access for a surgical portal which is inserted into the patient's body to permit viewing of the surgical site or for the insertion of instruments used in performing the surgical procedure. The surgical portal may be in the form of a trocar cannula assembly incorporating an outer cannula and an obturator which is positioned in the outer cannula. The obturator includes a sharpened point or tip which is used create a path to the surgical site. The obturator is then removed leaving the cannula in place to maintain access to the surgical site. Several incisions may be made to provide numerous access ports to the surgical objective, and once the cannulas are in place, various surgical instruments such as scissors, dissectors, retractors or the like, may be inserted by a surgeon to perform the surgery. Typically, a scope is used to view the area directly, or a miniature camera is used to display the surgical site on a video monitor in the operating room.

In order to maintain the cannula within the incision, it has been known to provide various mechanisms such as threaded cannulas, external sleeves, expandable members, balloons, etc. which engage the tissue surrounding the incision to prevent undesired removal of the cannula. However, such known mechanisms are generally complex in nature. Moreover, these mechanisms often are potentially invasive to the surrounding tissue thereby increasing the likelihood of undesired tissue tear which consequently increases patient trauma and recovery time.

SUMMARY

Accordingly, the present disclosure is directed to further improvements in the field of surgical portals. In one preferred embodiment, a surgical portal apparatus for permitting introduction of a surgical object within tissue includes a portal member defining a longitudinal axis and having leading and trailing ends. The portal member includes an outer wall defining a longitudinal opening dimensioned for reception of a surgical object. At least one projection is disposed on the outer wall of the portal member and extends in at least a radial direction relative to the longitudinal axis. The at least one projection is dimensioned and configured for engaging tissue to resist movement of the portal member within tissue. The at least one projection defines a recess dimensioned for receiving tissue portions adjacent thereto. Preferably, a plurality of projections is spaced about the outer wall of the portal member. At least two of the projections are circumferentially spaced relative to the longitudinal axis and/or at least two of the projections are longitudinally spaced relative to the longitudinal axis.

The at least one projection defines a leading surface and a trailing surface. The leading surface is dimensioned to permit passage of the portal member in a first direction corresponding to an insertion direction. The trailing surface is dimensioned to engage tissue upon movement of the portal member in a second direction corresponding to a removal direction to thereby resist movement of the portal member in the second direction and facilitate retention of the portal member in tissue. The at least one projection defines an opening adjacent the trailing surface and in communication with the open internal cavity. The at least one projection defines one of a generally arcuate cross-section and generally v-shaped cross-section. The at least one projection preferably terminates in an apex adjacent the leading surface.

The leading surface of the at least one projection is arranged at a leading angle relative to the longitudinal axis of the access member while the trailing surface of the at least one projection is arranged at a trailing angle relative to the longitudinal axis. The trailing angle of the trailing surface is greater than the leading angle of the leading surface. The leading surface of the at least one projection is obliquely arranged relative to the longitudinal axis at an angle ranging from about 5° to about 45°. The trailing angle of the trailing surface ranges from 30° to about 90°.

The portal member may be a cannula having the longitudinal opening and being adapted to receive surgical instrumentation. Alternatively, the portal member is adapted to receive a surgeon's hand or arm through the longitudinal opening.

In another preferred embodiment, a surgical cannula assembly includes a cannula housing and a cannula sleeve extending from the cannula housing. The cannula sleeve defines a longitudinal axis, and has proximal and distal ends. The cannula sleeve includes an outer wall defining a longitudinal opening therethrough adapted to receive surgical instrumentation to permit performance of a surgical task with the surgical instrumentation. A plurality of anchoring projections is spaced about the outer wall of the cannula sleeve. At least one of the anchoring projections defines an internal cavity and has an opening in communication with the internal cavity adapted to permit tissue to pass therethrough to be captured within the internal cavity, to thereby facilitate securement of the at least one anchoring projection and retention of the cannula sleeve relative to the tissue. Preferably, each of the anchoring projections defines an internal cavity and an opening in communication with the internal cavity. The anchoring projections each define a distal leading surface and a proximal trailing surface. The leading surface is obliquely arranged relative to the longitudinal axis and dimensioned to permit passage of the cannula sleeve in a first direction corresponding to an insertion direction. The trailing surface is dimensioned to engage tissue upon movement of the cannula sleeve in a second direction corresponding to a removal direction to thereby resist movement of the cannula sleeve in the second direction and facilitate retention of the cannula sleeve in tissue. The trailing surface of each anchoring projection defines the opening in communication with the internal cavity. The at least one anchoring projection defines one of an arcuate cross-section and a generally v-shaped cross-section. At least two of the anchoring projections are longitudinally spaced about the cannula sleeve.

BRIEF DESCRIPTION OF THE DRAWING(S)

Preferred embodiments of the present disclosure will be better appreciated by reference to the drawings wherein:

FIG. 3 is a cross-sectional view taken along the lines 3-3 of FIG. 2 further illustrating the anchoring projections in accordance with the embodiment of FIGS. 1-2;

FIG. 4 is a view similar to the view of FIG. 3 illustrating an alternate embodiment of the anchoring projections;

DETAILED DESCRIPTION OF THE PREFERRED EMBODIMENT(S)

Figure 1:
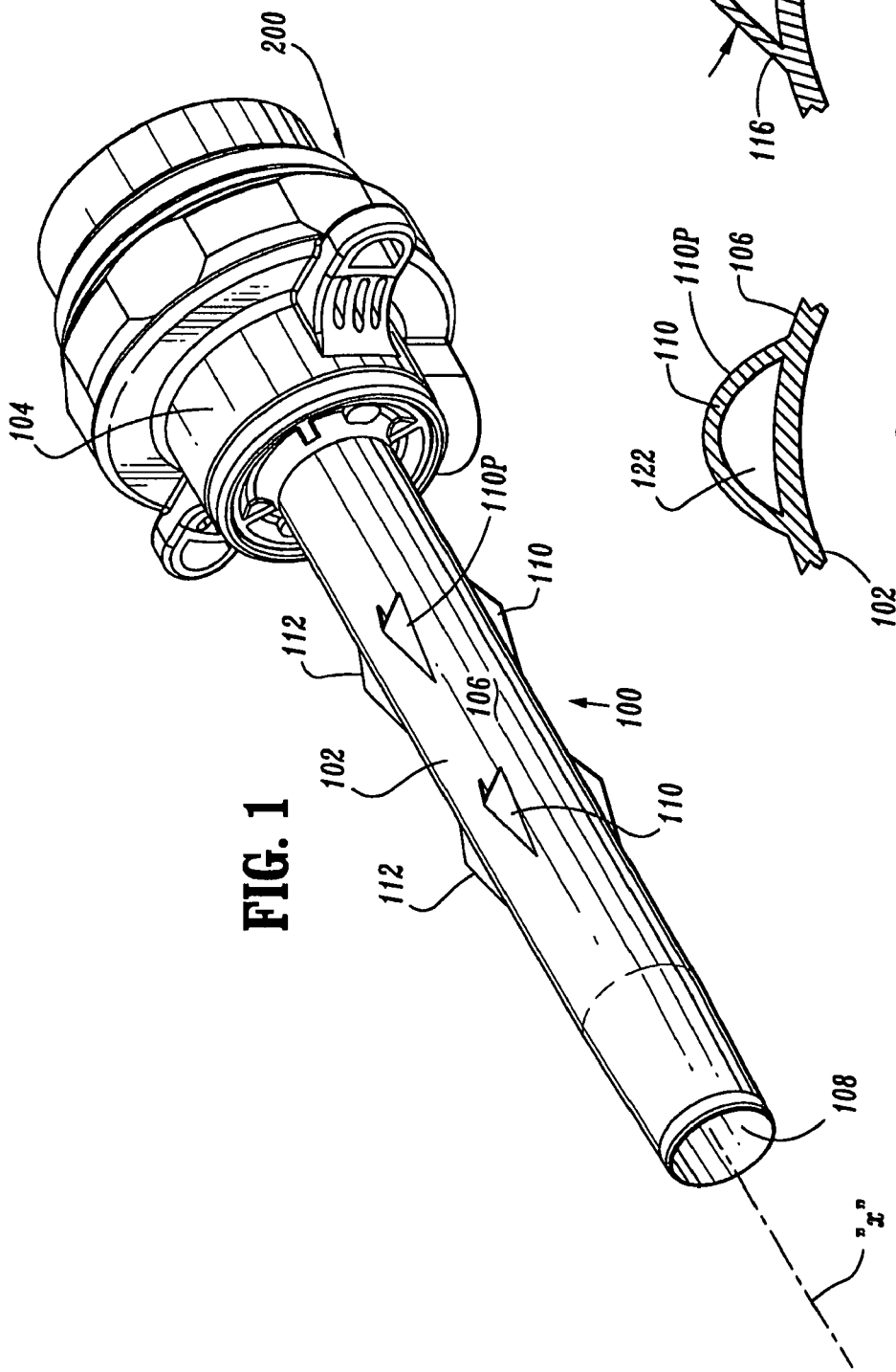
FIG. 1 is a perspective view of a surgical portal in the form of a cannula in accordance with the principles of the present disclosure.

Preferred embodiment(s) of the apparatus of the present disclosure will now be described in detail with reference to the drawings wherein like reference numerals identify similar or like elements throughout the several views. As used herein, the term "distal" refers to that portion which is further from the user, while the term "proximal" refers to that portion which is closest to the user.

The surgical portal of the present disclosure provides access to an underlying body cavity to permit the introduction of surgical objects and/or instrumentation for performing a surgical procedure. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation".

The surgical portal may be in the form of a trocar or cannula adapted for permitting introduction of the aforementioned instrumentation. Alternatively, the surgical portal may be a hand access apparatus used for receiving a physician's arm or hand during a hand-assisted laparoscopic surgical procedure.

Figure 2:
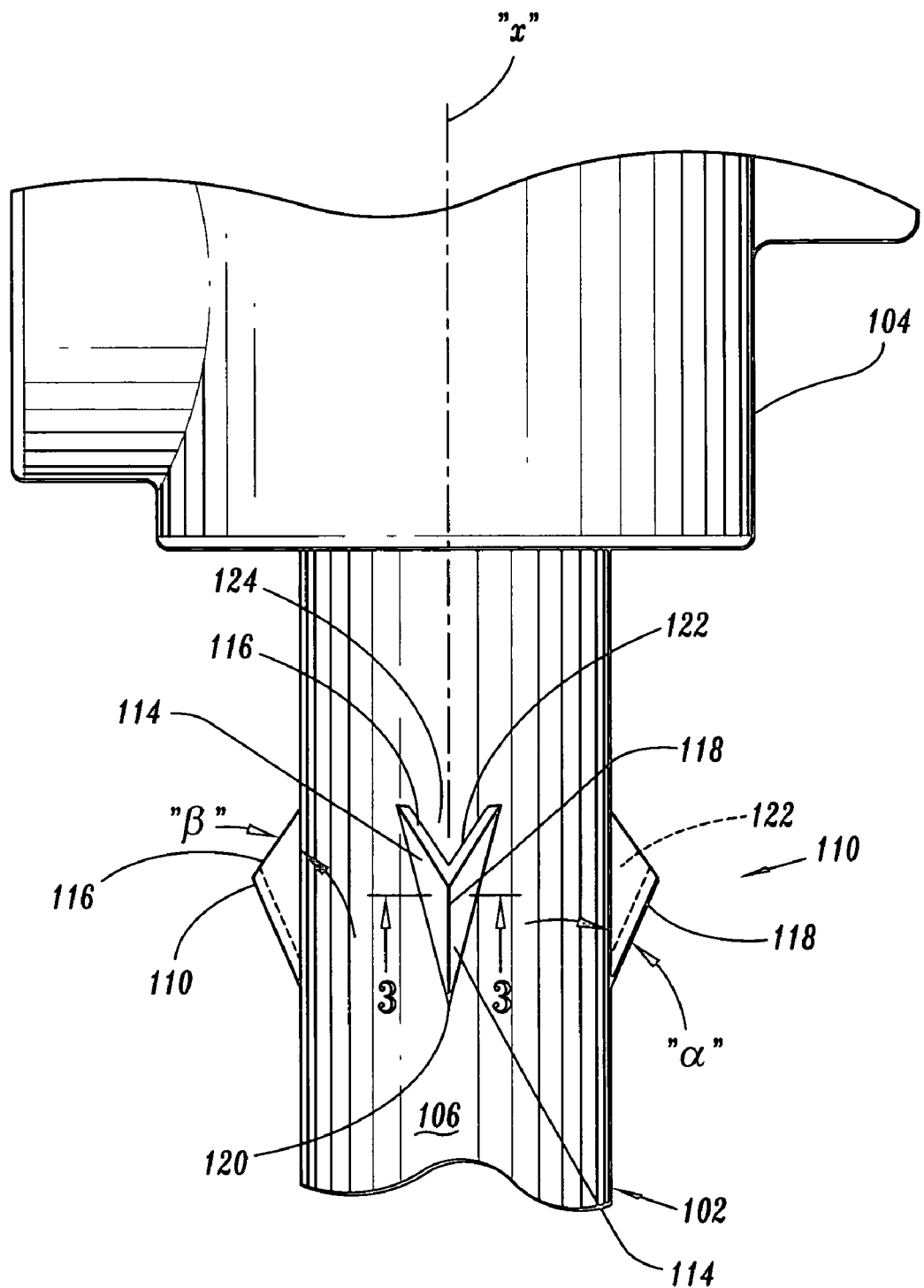
FIG. 2 is an elevation view of the cannula in accordance with the embodiment of FIG. 1, illustrating the anchoring projections for securing the cannula within a tissue site.

Referring now to the drawings, in which like reference numerals identify identical or substantially similar parts throughout the several views, FIGS. 1-3 illustrate the surgical portal in accordance with a preferred embodiment of the present disclosure. Surgical portal may be a trocar or cannula suitable for the intended purpose of accessing a body cavity, and defines a passageway permitting introduction of instruments therethrough. Surgical portal or cannula assembly 100 is particularly adapted for use in laparoscopic surgery where the peritoneal cavity is insufflated with a suitable gas, e.g., $CO_2$, to raise the cavity wall from the internal organs therein. Cannula assembly 100 is typically used with an obturator assembly (not shown) which may be blunt, a non-bladed, or a sharp pointed instrument positionable within the passageway of the cannula 100. The obturator assembly is utilized to penetrate the abdominal wall or introduce the cannula assembly 100 through the abdominal wall, and then subsequently is removed from the cannula assembly 100 to permit introduction of the surgical instrumentation utilized to perform the procedure through the passageway.

Cannula assembly 100 includes cannula sleeve 102 and cannula housing 104 mounted to an end of the sleeve 202. Cannula sleeve 102 defines a longitudinal axis "x" extending along the length of sleeve 102. Cannula sleeve 102 includes outer wall 106 defining internal longitudinal passage 108. Longitudinal passage 108 is dimensioned to permit passage of surgical instrumentation. Cannula sleeve 102 may be formed of stainless steel or other rigid materials such as a polymeric material or the like. Cannula sleeve 102 may be clear or opaque. The diameter of cannula sleeve 102 may vary, but, typically ranges from about 4.5 to about 15 mm.

Cannula sleeve 102 includes a plurality anchoring projections 110 spaced about outer wall 106. In one preferred embodiment, at least two longitudinally spaced rows 112 of anchoring projections 110 are provided. Each row 112 incorporates at least two, three, four or more anchoring projections 110 radially and preferably equidistally spaced about outer wall 106 at a predetermined angular spacing. For example, in an embodiment having two anchoring projections 110 in each row 112, the anchoring projections 112 may be separated by an angle of about 180°. With embodiments having three or four anchoring projections 110 in each row 112, the anchoring projections 110 may be separated by angles of about 120° and 90° respectively.

Anchoring projections 110 each define substantially planar leading or distal surfaces 114 and trailing or proximal surfaces 116. Leading surfaces 114 preferably intersect each other along edge or line of intersection 118 at a predetermined angle "?" (FIG. 3) ranging from about 300 to about 90°. The line of intersection 118 of leading surfaces 114 is arranged at a relatively small leading acute angle "a" (FIG. 2) relative to longitudinal axis "x" to define a general v-shaped cross-section. Angle "a" may range from about 5° to about 45° preferably about 5° to about 30°. Leading surfaces 114 also taper inwardly in the distal or leading direction to meet at apex 120. The aforedescribed configuration of leading surfaces 114 provides a narrow or reduced profile for anchoring projections 110. The reduced profile facilitates advancement of sleeve 102 and anchoring projections 110 relative to tissue. In an alternative arrangement depicted in FIG. 4, leading surface 114 may define a continuous arcuate or convex arrangement which tapers inwardly to define an apex. In this embodiment of FIG. 4, anchoring projections 110 defines an arcuate cross-section.

Trailing surfaces 116 taper inwardly toward each other in the distal direction to intersect along line of intersection 118. Trailing surfaces 116 are arranged at an acute trailing angle "β" relative to longitudinal axis "x". Angle "β" may range from about 30° to about 90° and is arranged to securely engage tissue and resist retropulsion or "backing out" of sleeve 102 relative to the tissue. Trailing angle "β" of trailing surfaces 116 is preferably greater than leading angle "a" of leading surfaces 114.

Figure 5:
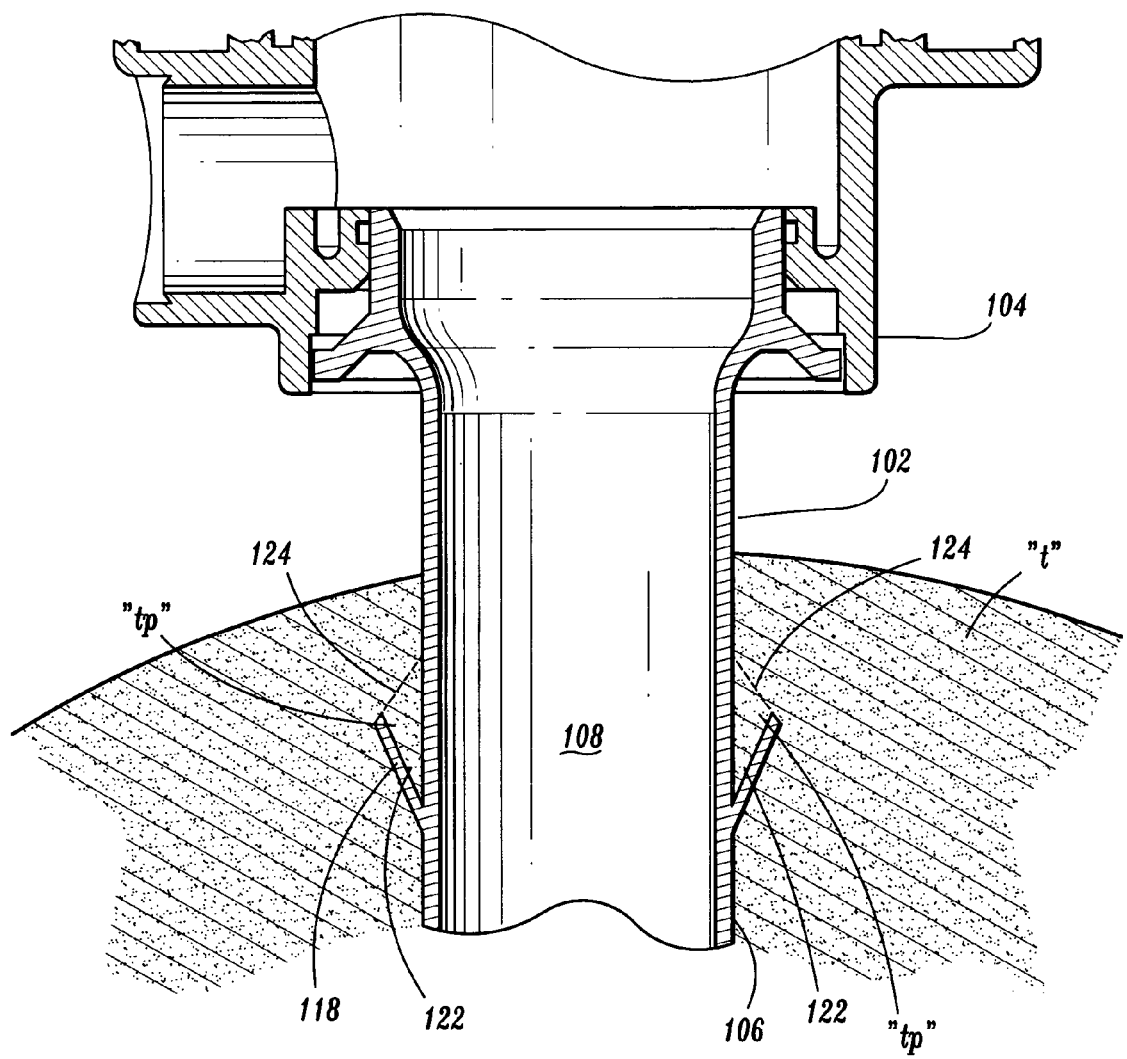
FIG. 5 is a partial side cross-sectional view of the cannula in accordance with the embodiment of FIGS. 1-3, illustrating the cannula positioned within tissue.

As best depicted in FIGS. 2 and 5, anchoring projections 110 further define open internal pocket, recess or cavity 122 within the peripheral boundary 110a of the respective anchoring projection 110. Internal pocket or cavity 122 is in communication with the exterior of sleeve 102 through opening 124 defined between trailing surfaces 116. Internal cavity 122 is intended to capture tissue portions "tp" which may be displaced by anchoring projections 110 of sleeve 102 when positioned within the tissue. (FIG. 5) The reception of tissue within internal cavity 122 serves to prevent egress of sleeve 102 relative to the tissue. Moreover, the combination of the tissue engagement capabilities presented by trailing surfaces 116 of anchoring projections 110 and the reception of tissue within internal cavity 122 provide a means to prevent slippage of sleeve 102 relative to tissue.

Referring again to FIG. 1, it is contemplated that cannula assembly 100 may have a valve or seal assembly 200 which may be mountable to housing 102, or incorporated into housing 102. Valve assembly 200 may include at least one valve or seal element adapted to form a seal about the inserted object to prevent release of insufflation gases through the cannula assembly 100. Valve or seal assembly 200 may also include a zero-closure valve (e.g., a flapper or duck bill valve) to close the axial opening of the apparatus in the absence of the object. One valve assembly suitable for this purpose is disclosed in commonly assigned U.S. Pat. No. 5,603,702 to Smith et al., the contents of which are hereby incorporated herein by reference. The '702 patent discloses, in certain embodiments, a valve assembly that may be adapted to mount to a housing of a cannula assembly through a detachable connection or the like including a bayonet coupling, friction fit, threaded connection or any other suitable connection known in the art.

Figure 6:
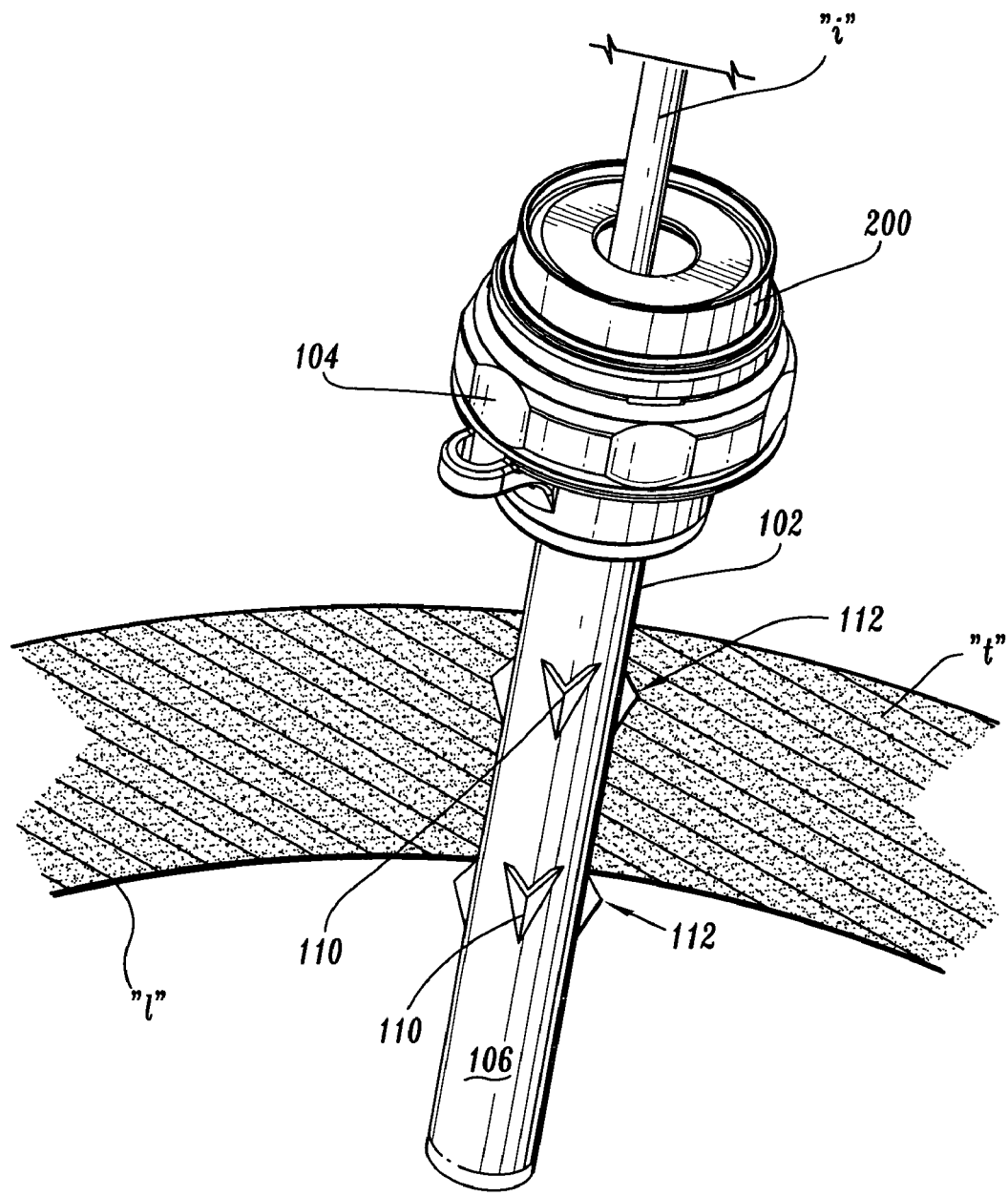
FIG. 6 is a view illustrating introduction of a surgical instrument within the cannula in accordance with the embodiment of FIGS. 1-3 and 5.

The operation of cannula assembly 100 will now be discussed. In a laparoscopic surgery, the peritoneal cavity is insufflated to raise the cavity wall to provide greater access to the tissue and organs within. A trocar may be is placed within cannula assembly 100 and advanced to extend the distal penetrating tip into the tissue. The trocar is used to puncture the abdominal wall as is conventional in the art. The trocar may then be removed if desired. Upon insertion of cannula sleeve 102 within the tissue "t" as depicted in FIG. 6, tissue portions "tp" adjacent anchoring projections 110 are captured within internal cavity 122 of the anchoring projections 110. (See again FIG. 5) This feature, along with the engagement of trailing surfaces 116 of anchoring projections 110 with the tissue, secures cannula sleeve 102 and prevents retropulsion of the cannula sleeve 102 even in the pressurized environment of the insufflated body cavity. It is noted that cannula sleeve 102 may be arranged such that the distal most row 112 of anchoring projections 110 engage the interior lining "l" of the abdominal wall. Thereafter, an object such as a surgical instrument "i" is introduced within the apparatus to perform the desired surgery. In further embodiments, the surgical portal is sized to receive a surgeon's hand, which is inserted into the body cavity.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical portal apparatus, which comprises: a portal member defining a longitudinal axis and having leading and trailing ends, the portal member including an outer wall defining a longitudinal opening dimensioned for reception and passage of a surgical object; and at least one projection mounted adjacent the outer wall of the portal member and extending radially outwardly from the outer wall, the at least one projection having an internal recess forming an enclosed pocket defined within a peripheral boundary of the at least one projection and the outer wall of the portal member and having an opening in communication with the internal recess, and being dimensioned for receiving tissue portions adjacent thereto, wherein the peripheral boundary of each of the at least one anchoring projection is defined by at least two substantially planar distal leading surfaces and at least two substantially planar proximal trailing surfaces, the leading and trailing surfaces extending distally and converging at a line of intersection that is remote the outer wall of the portal member, the leading surfaces also converging at an apex that is proximate the outer wall of the portal member such that the pocket is of diminishing tissue passing capacity as the pocket extends from the line of intersection to the apex.

2. The surgical portal apparatus according to claim 1, including a plurality of projections spaced about the outer wall of the portal member.

3. The surgical portal apparatus according to claim 2, wherein at least two of the projections are circumferentially spaced relative to the longitudinal axis.

4. The surgical access apparatus according to claim 2, wherein at least two of the projections are longitudinally spaced relative to the longitudinal axis.

5. The surgical portal apparatus according to claim 1, wherein each leading surface is dimensioned to permit passage of the portal member in a first direction corresponding to an insertion direction, and each trailing surface is dimensioned to engage tissue upon movement of the portal member in a second direction corresponding to a removal direction to thereby resist movement of the portal member in the second direction and facilitate retention of the portal member in tissue.

6. The surgical portal apparatus according to claim 5, wherein the at least one projection defines a generally v-shaped cross-section.

7. The surgical portal apparatus according to claim 5, wherein each leading surface of the at least one projection is arranged at a leading angle relative to a longitudinal axis of the portal member and wherein each trailing surface of the at least one projection is arranged at a trailing angle relative to the longitudinal axis, the trailing angle of each trailing surface being greater than the leading angle of each leading surface.

8. The surgical portal apparatus according to claim 7, wherein the leading angle of the at least one projection is an angle ranging from about 5° to about 45°.

9. The surgical access apparatus according to claim 8, wherein the trailing angle of each trailing surface ranges from about 30° to about 90°.

10. The surgical access apparatus according to claim 1, wherein the portal member is a cannula, the cannula having the longitudinal opening and being adapted to receive surgical instrumentation.

11. The surgical access apparatus according to claim 1, wherein the portal member is adapted to receive a surgeon's hand or arm through the longitudinal opening.

12. A surgical cannula assembly, which comprises: a cannula housing; a cannula sleeve extending from the cannula housing, the cannula sleeve defining a longitudinal axis, and having proximal and distal ends, the cannula sleeve having an outer wall defining a longitudinal opening therethrough adapted to receive surgical instrumentation to permit performance of a surgical task with the surgical instrumentation; and a plurality of anchoring projections extending contiguously from the outer wall of the cannula sleeve, at least one of the anchoring projections defining an internal cavity forming an enclosed pocket within an outer boundary of the at least one anchoring projection and the outer wall of the portal member, and having an opening in communication with the internal cavity adapted to permit tissue to pass therein and to be captured within the internal cavity, to thereby facilitate securement of the at least one anchoring projection and retention of the cannula sleeve relative to the tissue, wherein the outer boundary of each of the anchoring projections is defined by at least two substantially planar distal leading surfaces and at least two substantially planar proximal trailing surfaces, the leading and trailing surfaces extending distally and converging at a line of intersection that is remote the outer sleeve of the cannula, the leading surfaces also converging at an apex that is proximate the outer sleeve of the cannula such that the pocket is of diminishing tissue passing capacity as the pocket extends from the line of intersection to the apex.

13. The surgical cannula assembly according to claim 12, wherein each leading surface is obliquely arranged relative to the longitudinal axis and dimensioned to permit passage of the cannula sleeve in a first direction corresponding to an insertion direction, and each trailing surface is dimensioned to engage tissue upon movement of the cannula sleeve in a second direction corresponding to a removal direction to thereby resist movement of the cannula sleeve in the second direction and facilitate retention of the cannula sleeve in tissue.

14. The surgical cannula assembly according to claim 13, wherein the trailing surfaces of each anchoring projection define the opening in communication with the internal cavity.

15. The surgical cannula assembly according to claim 14, wherein the at least one projection defines a generally v-shaped cross-section.

16. The surgical cannula assembly according to claim 15, wherein at least two of the anchoring projections are longitudinally spaced about the cannula sleeve.

17. The surgical cannula assembly according to claim 12, including first and second sets of anchoring projections being longitudinally displaced relative to the longitudinal axis.

18. The surgical cannula assembly according to claim 17, wherein each of the first and second sets includes at least two anchoring projections.

* * * * *